United States Patent
Phillips et al.

(10) Patent No.: US 11,583,802 B2
(45) Date of Patent: Feb. 21, 2023

(54) PHOTOCATALYTIC OXIDATION MEDIA AND SYSTEM

(71) Applicant: Zentox Corporation, Newport News, VA (US)

(72) Inventors: Joe D. Phillips, Barhamsville, VA (US); Stephen P. Axtell, Charlotte, NC (US)

(73) Assignee: ZENTOX CORPORATION, Newport News, VA (US)

( * ) Notice: Subject to any disclaimer, the term of this patent is extended or adjusted under 35 U.S.C. 154(b) by 0 days.

(21) Appl. No.: 15/048,938

(22) Filed: Feb. 19, 2016

(65) Prior Publication Data
US 2016/0166987 A1    Jun. 16, 2016

Related U.S. Application Data

(62) Division of application No. 13/963,988, filed on Aug. 9, 2013, now abandoned.

(60) Provisional application No. 61/681,615, filed on Aug. 10, 2012.

(51) Int. Cl.
| | |
|---|---|
| *B01D 53/86* | (2006.01) |
| *A61L 9/20* | (2006.01) |
| *B01D 53/88* | (2006.01) |
| *B01J 21/06* | (2006.01) |
| *B01J 23/38* | (2006.01) |
| *B01J 35/00* | (2006.01) |
| *C02F 1/32* | (2023.01) |

(52) U.S. Cl.
CPC .......... *B01D 53/8687* (2013.01); *A61L 9/205* (2013.01); *B01D 53/885* (2013.01); *B01J 21/063* (2013.01); *B01J 23/38* (2013.01); *B01J 35/004* (2013.01); *B01D 2255/10* (2013.01); *B01D 2255/102* (2013.01); *B01D 2255/20707* (2013.01); *B01D 2255/802* (2013.01); *B01D 2257/708* (2013.01); *B01D 2258/06* (2013.01); *C02F 1/325* (2013.01); *C02F 2305/10* (2013.01)

(58) Field of Classification Search
CPC ... B01D 53/8687; B01D 53/885; A61L 9/205; B01J 21/063; B01J 23/38; B01J 35/004
See application file for complete search history.

(56) References Cited

U.S. PATENT DOCUMENTS

| | | | |
|---|---|---|---|
| 5,273,565 A | 12/1993 | Milligan et al. | |
| 5,766,455 A | 6/1998 | Berman et al. | |
| 5,790,934 A | 8/1998 | Say et al. | |
| 5,834,069 A | 11/1998 | Berman et al. | |
| 5,933,702 A * | 8/1999 | Goswami | A61L 9/205 422/186.3 |
| 5,948,355 A | 9/1999 | Fujishima et al. | |
| 6,063,343 A | 5/2000 | Say et al. | |
| 6,315,963 B1 | 11/2001 | Speer | |
| 6,419,792 B1 * | 7/2002 | Nishibori | B02C 13/22 162/181.4 |

(Continued)

FOREIGN PATENT DOCUMENTS

WO    WO 98/52672    11/1998

*Primary Examiner* — Regina M Yoo
(74) *Attorney, Agent, or Firm* — Lewis Roca Rothgerber Christie LLP

(57) ABSTRACT

A filter configured to photocatalytically oxidize target compounds in an air stream includes a support structure having an air permeability greater than approximately 155 CFM/ft² and a photocatalyst supported by the support medium.

7 Claims, 8 Drawing Sheets

(56) References Cited

U.S. PATENT DOCUMENTS

| | | | |
|---|---|---|---|
| 6,673,207 B1* | 1/2004 | Nishibori | D21B 1/32 |
| | | | 162/181.4 |
| 7,074,369 B2 | 7/2006 | Tabatabaie-Raissi et al. | |
| 7,740,810 B2 | 6/2010 | Hay et al. | |
| 7,820,100 B2 | 10/2010 | Garfield et al. | |
| 8,034,146 B2* | 10/2011 | Kobori | B01D 46/521 |
| | | | 55/528 |
| 2001/0050218 A1 | 12/2001 | Tabatabaie-Raissi et al. | |
| 2002/0106313 A1 | 8/2002 | Tabatabaie-Raissi et al. | |
| 2003/0085111 A1 | 5/2003 | Tabatabaie-Raissi et al. | |
| 2004/0262217 A1 | 12/2004 | Mori et al. | |
| 2006/0124442 A1* | 6/2006 | Valpey, III | A61L 9/205 |
| | | | 204/157.15 |
| 2007/0020158 A1* | 1/2007 | Kuramoto | C02F 1/4674 |
| | | | 422/186.3 |
| 2007/0128434 A1 | 6/2007 | Motoda et al. | |
| 2007/0199450 A1* | 8/2007 | Wiser | B03C 3/64 |
| | | | 96/69 |
| 2010/0135864 A1 | 6/2010 | Taniguchi et al. | |
| 2011/0268961 A1* | 11/2011 | Manabe | B29C 55/04 |
| | | | 428/319.3 |
| 2012/0117919 A1* | 5/2012 | Tokuhiro | B01J 33/00 |
| | | | 53/400 |

* cited by examiner

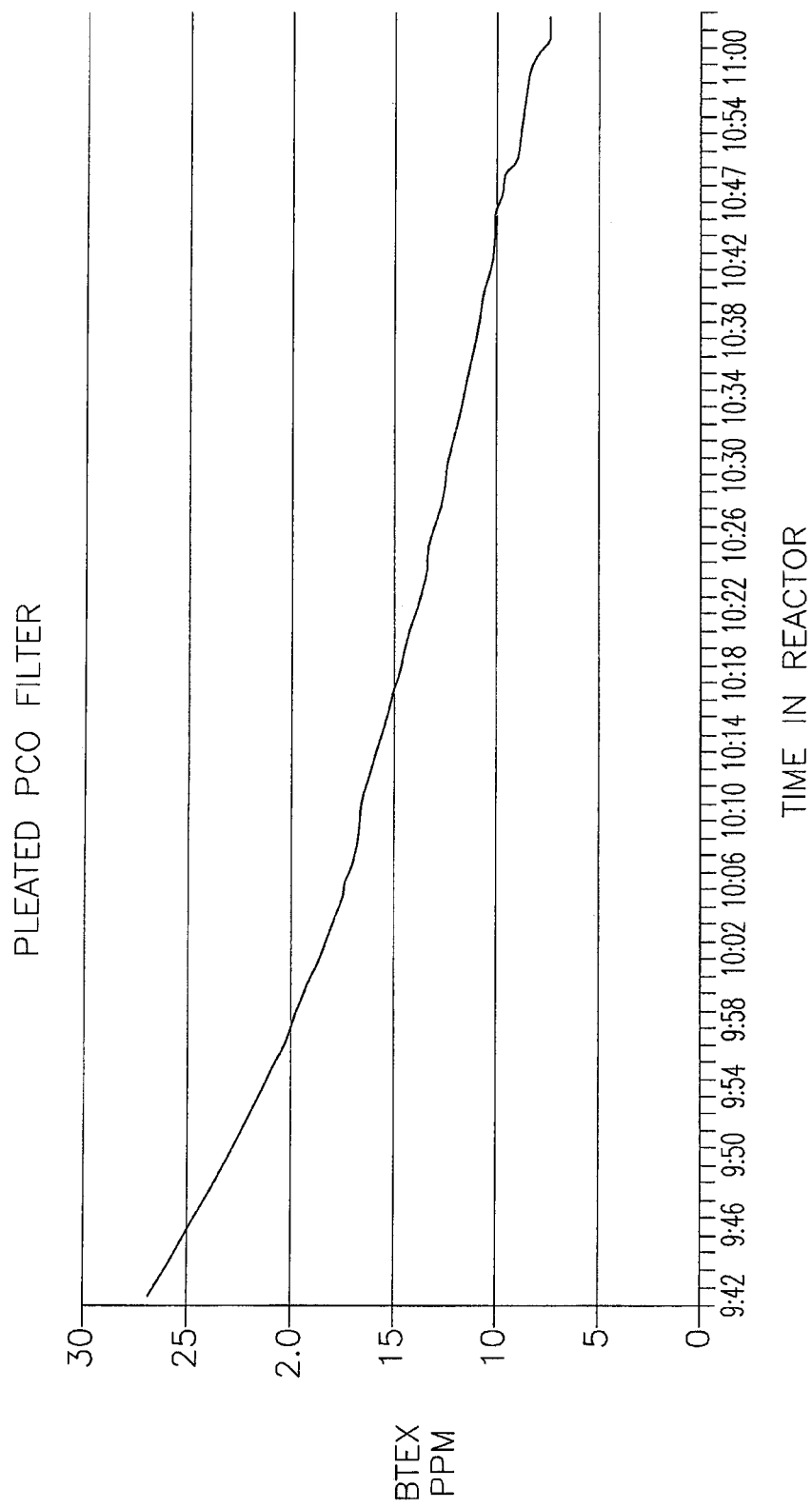

PHOTOCATALYTIC OXIDATION MEDIA AND SYSTEM

CROSS-REFERENCE TO RELATED APPLICATIONS

This application is a divisional of U.S. application Ser. No. 13/963,988, filed Aug. 9, 2013, which claims priority to and the benefit of U.S. Provisional Application No. 61/681,615, filed Aug. 10, 2012, the entire contents of both of which are incorporated herein by reference.

FIELD OF THE INVENTION

The present invention relates to photocatalytic oxidation media and systems, and more particularly to a photocatalytic medium and system having a photocatalyst supported on a medium.

BACKGROUND

It has been demonstrated that photocatalytic oxidation can effectively degrade compounds in a fluid stream (U.S. Pat. No. 5,766,455). It has further been demonstrated that when a semiconductor catalyst utilized in such a photocatalytic oxidation reactor is metalized in situ the overall performance of the process can be significantly enhanced in the degradation of certain compounds (U.S. Pat. No. 5,834,069).

One of the limiting factors of the photocatalytic oxidation reactor described in U.S. Pat. No. 5,766,455 is that media used to support the semiconductor catalyst comprise a plurality of densely-packed fibers. While air can pass through such a densely-packed medium, the volume of air passable through it can limit the economic viability of the reactor. High pressure drops caused by densely-packed media require significantly high levels of energy to drive air through the media. Such high pressure drops can make photocatalytic oxidation reactors that utilize densely-packed media economically impractical.

SUMMARY

The present invention utilizes photocatalytic oxidation media consisting of loosely-packed fibers or other suitable material as a support structure for semiconductor catalyst in the photocatalytic degradation of target compounds. One potential benefit of using loosely-packed media is that they allow air to pass more easily, creating less pressure drop, and therefore consuming significantly less energy. Also, because indoor air treatment systems are essentially "closed loop" in the sense that air is constantly recycled through them, loosely-packed media enable more contact time for a given target compound to be exposed to UV activated semiconductor catalyst over a given period. While loosely-packed media actually utilize less catalyst than densely-packed media due to the difference in the number of available fibers or other surface structures to which catalyst can be bound, they can also facilitate target compound and catalyst contact resulting in potentially greater target compound degradation.

More specifically, media and systems of the invention have a photocatalytic support structure having an air permeability of more than approximately 155 CFM/ft² and a photocatalyst supported by the support medium. In one embodiment, the system includes a photocatalytic reactor having an interior, a support structure within the reactor and having an air permeability of more than approximately 155 CFM/ft² and a photocatalyst supported by the support structure. In other embodiments, the air permeability of the support structure may be at least approximately 200 CFM/ft² or at least approximately 247 CFM/ft².

The present disclosure is also directed to a method of oxidizing a concentration of target compounds in an airstream. In one embodiment, the method includes passing the airstream through a filter having a photocatalyst on a support structure and irradiating the photocatalyst on the support structure with an ultraviolet light source. In one embodiment, the filter is configured to reduce the concentration of target compounds in the airstream at a rate of approximately 0.05 ppm/minute. In another embodiment, the filter is configured to reduce the concentration of target compounds in the airstream at a rate of approximately 0.24 ppm/minute. In one embodiment, the method includes passing the airstream through the filter at a volumetric flow rate of approximately 182 L/min. In one embodiment, the support structure is a fibrous matte and the photocatalyst is titanium dioxide. In one embodiment, the support structure is pleated. In one embodiment, the support structure has an air permeability of less than approximately 155 CFM/ft². In another embodiment, the support structure has an air permeability of approximately 247 CFM/ft².

This summary is provided to introduce a selection of concepts that are further described below in the detailed description. This summary is not intended to identify key or essential features of the claimed subject matter, nor is it intended to be used in limiting the scope of the claimed subject matter.

BRIEF DESCRIPTION OF THE DRAWINGS

The above and other features of the present invention may be better understood from the following description, taken together with the accompanying drawings, wherein similar reference characters refer to similar elements and in which:

FIG. 8 is a graph showing testing results related to the performance of the pleated PCO filter illustrated in FIG. 6.

DETAILED DESCRIPTION

The present disclosure relates to a photocatalytic oxidation (PCO) air treatment system having a photocatalyst supported in a reaction zone by a loosely-packed medium through which an airstream containing target compounds, such as volatile organic compounds, is passed. Such a system may operate in a substantially "closed loop" manner such that the target compounds repeatedly contact the photocatalyst to facilitate degradation (i.e., oxidation) thereof.

Figure 1:
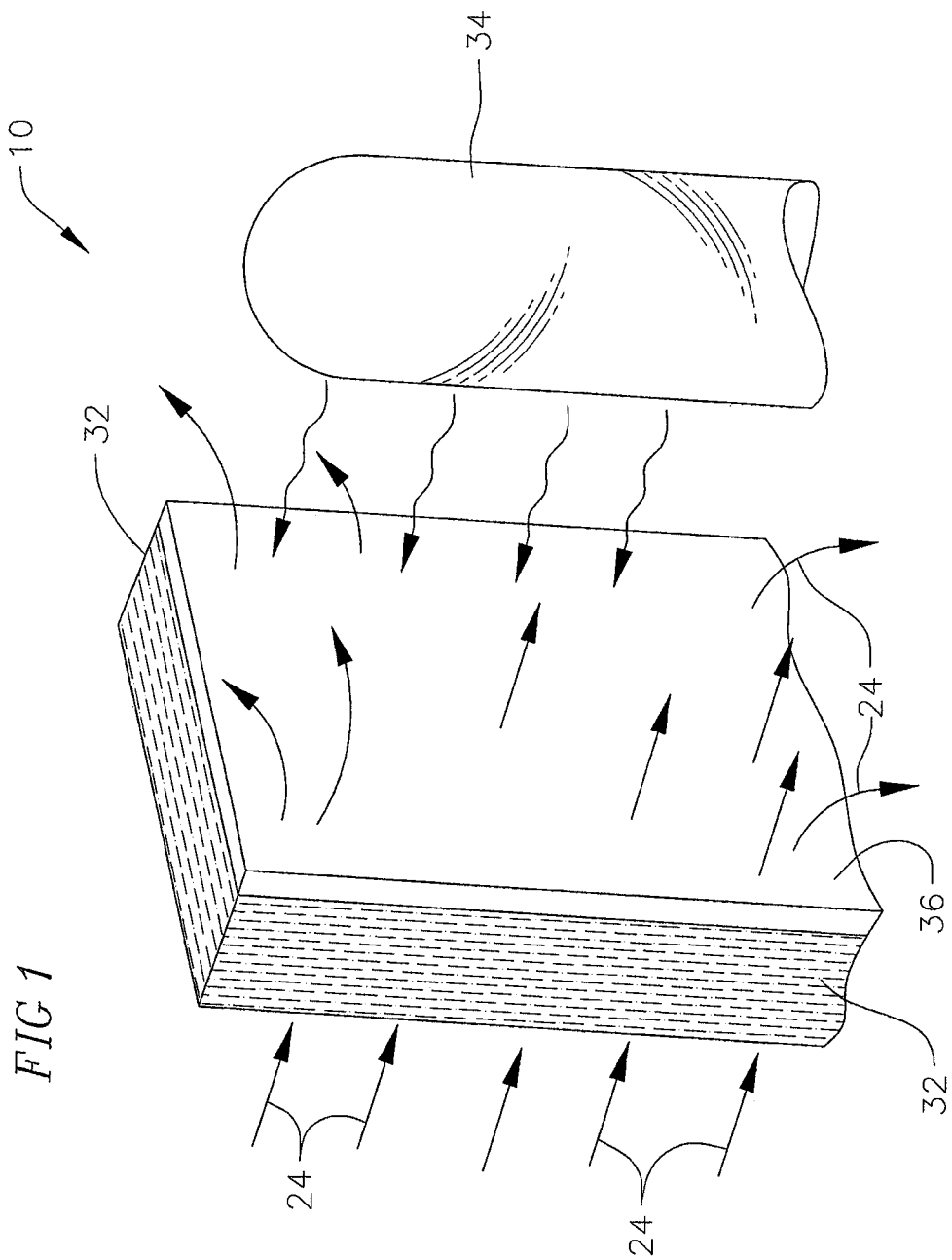
FIG. 1 is a stylized perspective view of a photocatalytic oxidation (PCO) filter according to one embodiment of the present disclosure having a support medium, a photocatalyst on the support medium, and an ultraviolet (UV) light source configured to irradiate the photocatalyst.
Figure 2:
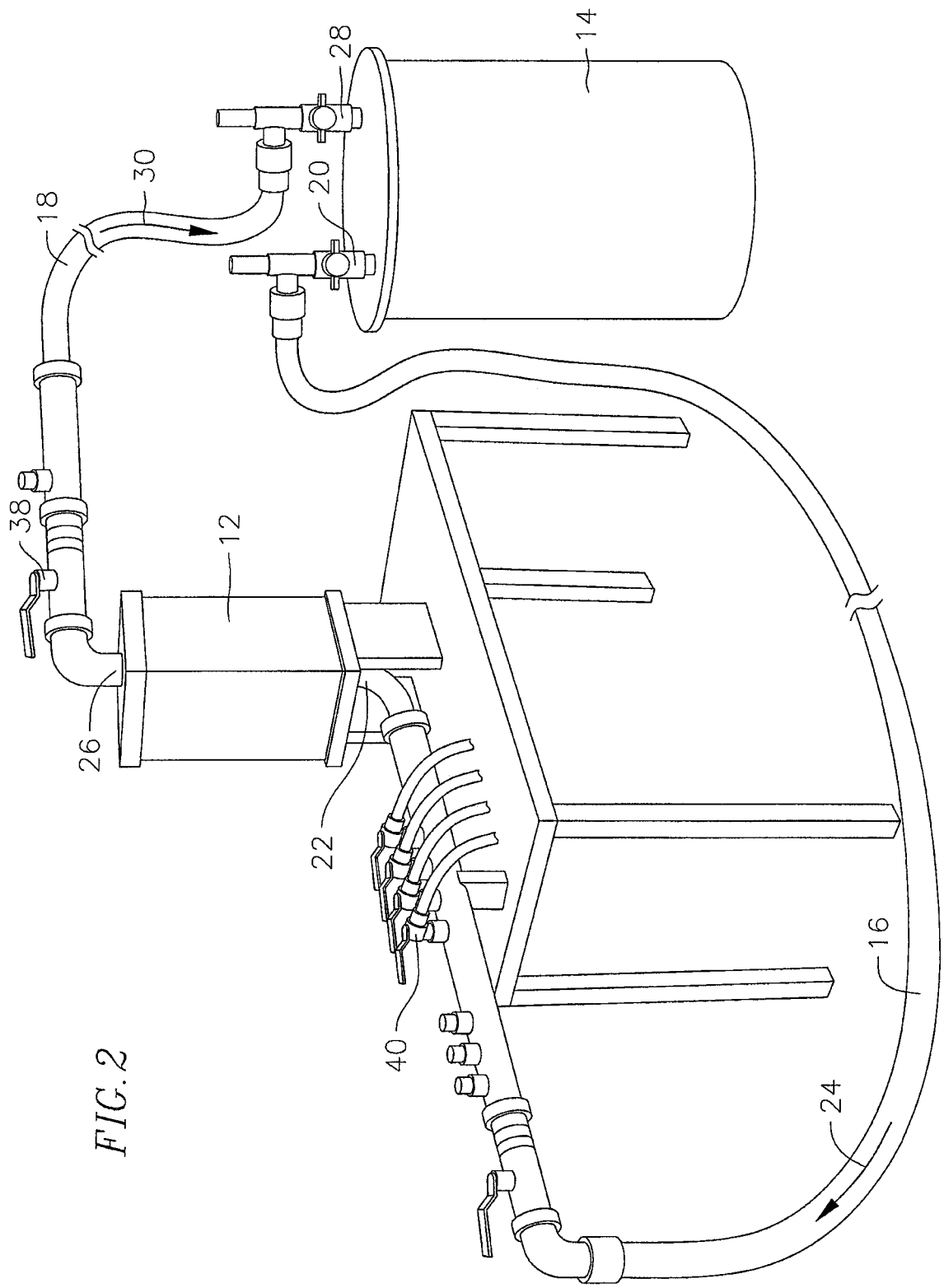
FIG. 2 is a perspective view of a closed-loop testing apparatus configured to test the efficacy of the various PCO filters of the present disclosure in degrading target compounds in an airstream.

With reference now to the embodiment illustrated in FIG. 1, a photocatalytic oxidation (PCO) filter 10 includes a support medium 32, a photocatalyst 36 attached to the support medium 32, and an ultraviolet (UV) light source 34 configured to irradiate the photocatalyst 36. The irradiation of the photocatalyst 36 with UV light produces hydroxyl radicals and super-oxide ions that are highly reactive with volatile organic compounds (VOCs), such as formaldehyde and ammonia. In this manner, the VOCs in the airstream are oxidized (i.e., degraded) as they are absorbed on the catalyst surface as the airstream passes through the PCO filter 10. The PCO filter 10 is housed in a reactor 12, as illustrated in FIG. 2. The support medium 32 may be a silica-based fibrous matte or other suitable support material to which the photocatalyst 36 is adhered. The photocatalyst 36 may be adhered to the support medium 32 in any suitable manner, such as, for example, as described in U.S. Pat. Nos. 5,766,455 and 5,834,069, the entire contents of both of which are hereby incorporated by reference for all purposes. The photocatalyst 36 on the support medium 32 may be a semiconductor catalyst such as a transition metal oxide, for example titanium dioxide or other suitable material. Additionally, the photocatalyst 36 may be metalized or non-metalized. The photocatalyst 36 may be metalized with any suitable metal such as, for example, a noble metal, such as platinum and/or palladium. The metal may be deposited on the photocatalyst 36, if desired, before the photocatalyst 36 is applied to the support medium 32.

With reference now to FIG. 2, a closed-loop testing apparatus is illustrated. The closed-loop testing apparatus is configured to repeatedly cycle an airstream through various embodiments of the PCO filters 10 of the present disclosure to test the efficacy of the PCO filters 10 at degrading target compounds, such as VOCs, within the airstream. In the illustrated embodiment, the closed-loop testing apparatus includes a photocatalytic reactor 12 connected to a tank 14 in a closed loop configuration by pipes 16 and 18. The pipe 16 carries air from an outlet 20 of the tank 14 to an inlet 22 of the reactor 12 in a feed airstream 24 for photocatalytic processing, and the pipe 18 returns processed air from an outlet 26 of the reactor 12 to an inlet 28 of the tank 14 in a return air stream 30. The photocatalytic reactor 12 houses the PCO filter 10 (i.e., the support medium 32, the photocatalyst 36 on the support medium 32, and the UV light source 34) as described above with reference to FIG. 1. Thus, the testing apparatus of the illustrated embodiment is a closed loop system capable of causing target compounds within the airstream 24 to repeatedly contact the photocatalyst 36, which is illuminated by the UV light source 34, resulting in those target compounds being efficiently and effectively degraded. In the illustrated embodiment, the tank 14 has a capacity of approximately 380 L and the testing apparatus has an overall capacity of approximately 440 L, although the tank 14 and the testing apparatus may have any other suitable volumetric capacities and still fall within the scope and spirit of the present disclosure. The closed-loop testing apparatus also includes an "OUT" sample port 38 located in pipe 18 downstream of the reactor 12 and an "IN" sample port 40 located in pipe 16 upstream of the reactor 12. The sample ports 38, 40 are configured to enable a user to measure the concentration of the target compounds (e.g., VOCs) in the airstream at predetermined time intervals. Additionally, each of the sample ports 38, 40 includes a ball valve configured to be opened to permit sampling of the airstream and subsequently closed to minimize the loss of the test air during sampling. In the illustrated embodiment, the reactor 12 is a stainless steel LeVOCC™ 100 photocatalytic oxidation indoor air treatment reactor unit manufactured by Zentox Corporation, although any other suitable reactors may be used. The bottom and top of the reactor 12 are sealed with rubber gaskets to ensure that the test airstream flows through the PCO filter in the reactor 12 with minimal losses.

As described in detail below, several tests were performed on various embodiments of the PCO filters of the present disclosure. In the first set of tests, a Toluene target compound was introduced into the closed-loop testing apparatus, and the performance of two different PCO filters (one having a densely-packed support medium 32 and the other having a loosely-packed support medium 32) in reducing the concentration of Toluene in the system were measured. As described below, the PCO filter having the loosely-packed support medium 32 outperformed the PCO filter having the densely-packed support medium 32. In a second set of tests, a benzene, toluene, ethylbenzene, and xylenes (BTEX) target compound was introduced into the closed-loop testing apparatus. The performance of two different PCO filters (one having a flat support medium 32 and the other having a pleated support medium 32) in reducing the concentration of the BTEX target compound were measured. As described below, the PCO filter having the pleated support medium 32 outperformed the PCO filter having the flat support medium 32.

Testing Methodology

The concentration of target compounds within the airstream 24, 30 of the closed-loop testing system ("Test Unit") were analyzed using a Rae Systems Multi-Rae Plus (Model PGM-50) Photo Ionization Detector (PID) equipped with a 10.6 eV lamp, calibrated with Isobutylene and a four (4) gas mixture of Hydrogen Sulfide, Carbon Monoxide, Methane and Oxygen. The PID analyzes concentrations of chemicals, including volatile organic compounds (VOCs), present in the airstream 24, 30. The PID was connected to either the "IN" or "OUT" sample ports 40, 38 and measurements were recorded at regular time intervals from the sample port. The ball valve on the sample port was closed after recording a measurement from the sample port to minimize the amount of target compounds which escape from the testing apparatus.

During the experiments, once the desired gas or vapor concentrations of the target compound (i.e., Toluene or BTEX) were reached through the introduction of gas or vapor mixture into the system, the system was closed and the airstream was allowed to re-circulate. The Reactor Unit 12 includes switch configured to allow the UV light 34 in the Reactor Unit 12 to be switched off. In order to achieve the desired concentration of target compounds in the airstream, the UV light was switched off while a fan (not shown) was left running to circulate the target compounds through the apparatus. Once the desired concentration of target compounds (i.e., Toluene or BTEX) was achieved, the system was allowed to run for five (5) minutes or until gas or vapor concentrations levels were confirmed to be stable. The UV light 34 was then switched on and the concentrations of the target compounds in the airstream were recorded at predetermined intervals. The results of these tests are described in detail below.

Toluene Test

Tests were conducted on two different PCO filters by introducing five (5) ml of Toluene into the Test Unit. The Toluene vapors were introduced to the Test Unit through a pre-mix chamber. Vapors were collected and mixed within the 380 L stainless steel tank and incoming gases were monitored using the calibrated PID. The 5 ml of Toluene brought the VOC concentration to approximately 5-6 ppm within the Test Unit. Once readings were stable, the system was allowed to circulate for additional five (5) minutes before the UV light was activated to irradiate the photocatalyst on the support medium. During these tests, the volumetric flow rate through the system was maintained at approximately 182 L/min (6.43 ft^3/min.). Each test began with a recorded measurement of Toluene at the "IN" sample port 40. Measurements were then recorded every ten (10) minutes from the "IN" sample port 40. Sampling was terminated at the 90 minute point for a total of ten data points.

In the first test, the reactor 12 contained a first PCO filter 10 having a densely-packed support medium with an air permeability rating ("APR") of less than approximately 155 $CFM/ft^2$. In the second test, the reactor 12 contained a different, second PCO filter 10 having a loosely-packed support medium 32 with an APR of approximately 247 $CFM/ft^2$. The term "loosely-packed" as used herein means that the support medium has a permeability to air of more than approximately 155 $CFM/ft^2$, and in some embodiments at least approximately 200 $CFM/ft^2$ or at least approximately 247 $CFM/ft^2$. The loosely-packed support medium 32 was also approximately 3/8 inch thicker than the densely-packed support medium. In particular, the PCO filter having a loosely-packed support medium was wrapped twice around a support structure housed within the reactor 12, whereas the PCO filter having the densely-packed support medium was only wrapped once around the support structure in the reactor 12. All other system components and settings were identical between the two tests (i.e., both the densely-packed and the loosely-packed support mediums 32 were coated with the same semiconductor catalyst (titanium dioxide and platinum), activated by the same UV lamps with the same intensity, and exposed to substantially the same concentration of the same target compound (Toluene)). Additionally, the support mediums 32 of the two different PCO filters were both comprised of a fiberglass matter that was coated by a process that permanently bonds titanium dioxide and platinum to the silica based media.

Figure 3:
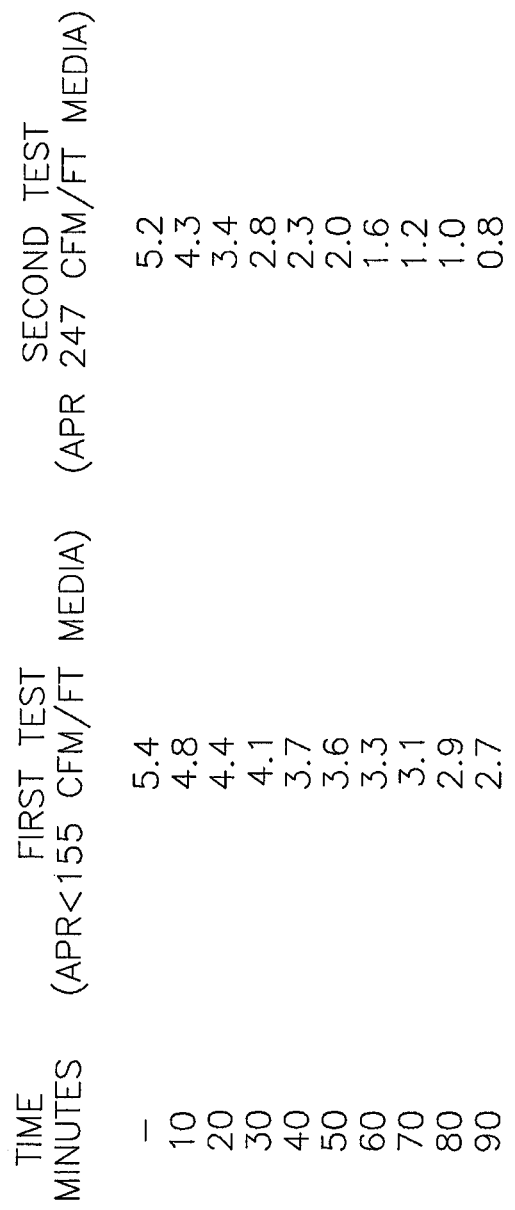
FIG. 3 is a table containing test data comparing the efficacy of a loosely-packed PCO filter and a densely-packed PCO filter in degrading Toluene in an airstream.
Figure 4:
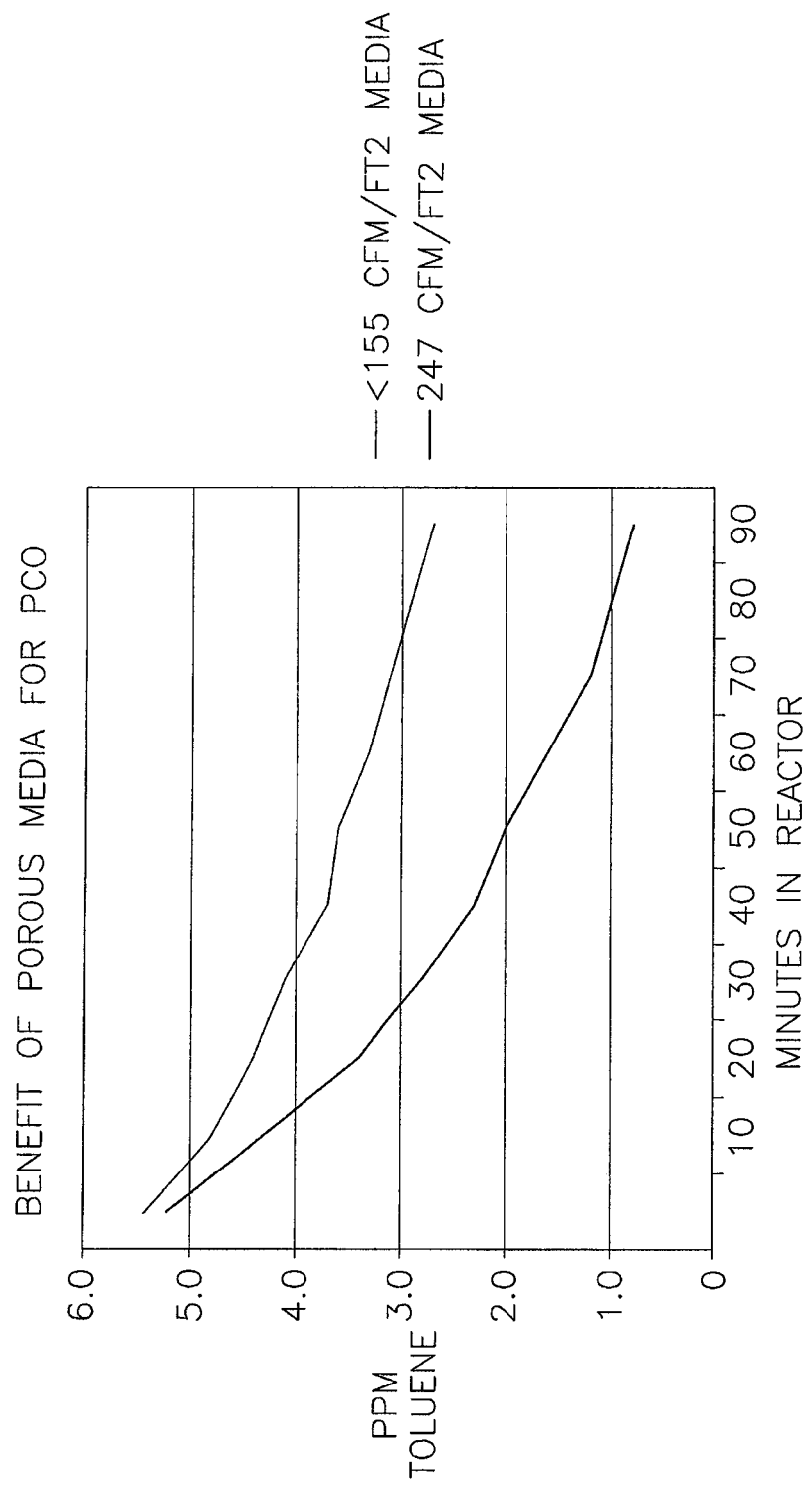
FIG. 4 is a graph plotting the data contained in the table of FIG. 3.

As illustrated in FIGS. 3 and 4, after circulating the airstream 24 through the Test Unit having the densely-packed PCO filter for approximately ninety (90) minutes, the concentration of Toluene in the system was reduced from approximately 5.4 parts-per-million ("ppm") to approximately 2.7 ppm (i.e., the concentration of Toluene in the system was reduced by approximately 50%). Accordingly, the densely-packed PCO filter reduced the concentration of Toluene in the system at a rate of approximately 0.030 ppm/minute.

In contrast, after circulating the airstream through the Test Unit having the loosely-packed PCO filter for approximately ninety (90) minutes, the concentration of toluene was reduced from approximately 5.2 parts-per-million ("ppm") to approximately 0.8 ppm (i.e., the concentration of toluene in the system was reduced by approximately 85%). Accordingly, the loosely-packed medium reduced the concentration of Toluene in the system at a rate of approximately 0.049 ppm/minute. Thus, the loosely-packed PCO filter is configured to reduce the concentration of Toluene in the system approximately 1.63 times faster than the densely-packed PCO filter (i.e., 63% percent faster).

Although not wishing to be bound by any particular theory, it is believed that the loosely-packed support medium (e.g., a support medium having an APR of approximately 247 $CFM/ft^2$) enables more photocatalytic sites on the PCO filter to be irradiated by the UV light source, which in turn results in the degradation (i.e., oxidation) of more target compounds within the airstream per minute than an otherwise equivalent PCO filter having a relatively denser-packed support medium (e.g., a support medium having an APR of less than approximately 155 $CFM/ft^2$). Additionally, due to the greater thickness of the loosely-packed support medium, it is believed that the PCO filter having a loosely-packed support medium is capable of supporting a greater amount of photocatalyst (e.g., titanium dioxide and platinum) than an otherwise equivalent PCO filter having a relatively denser-packed support medium. Thus, the greater number of active catalytic sites on the loosely-packed PCO filter enables a loosely-packed PCO filter to degrade/oxidize target compounds within the airstream more quickly than a relatively denser-packed PCO filter. Moreover, even though the loosely-packed medium was 3/8 inch thicker than the densely-packed support medium, the air permeability of the loosely-packed medium (i.e., 247 $CFM/ft^2$) was greater than the air permeability of the densely-packed medium (i.e., less than 155 $CFM/ft^2$), and thus the airstream is able to circulate through the closed-loop testing apparatus having the loosely-packed medium more rapidly than the densely-packed medium. The higher rate of circulation through the PCO filter having the loosely-packed medium exposes the target compounds in the airstream to the active photocatalyst sites on the loosely-packed medium more frequently, and thus the target compounds in the airstream are oxidized more rapidly (i.e., the airstream experiences less of a pressure drop across the loosely-packed medium, and thus the airstream circulates more rapidly through the closed-loop apparatus and encounters the active photocatalyst sites on the loosely-packed PCO filter more frequently).

BTEX Test

Figure 5:
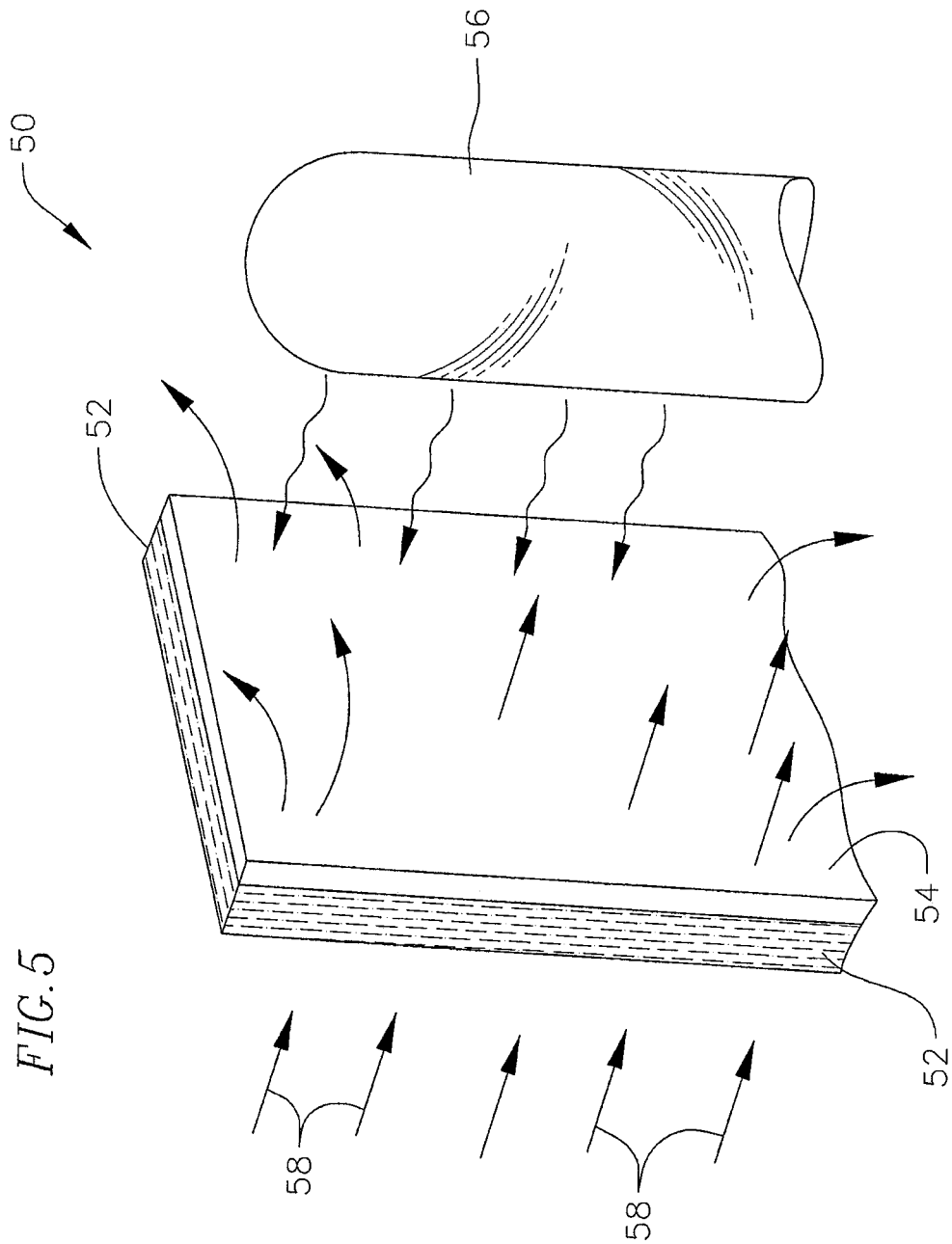
FIG. 5 is a stylized perspective view of a flat PCO filter and a UV light source according to one embodiment of the present disclosure.
Figure 6:
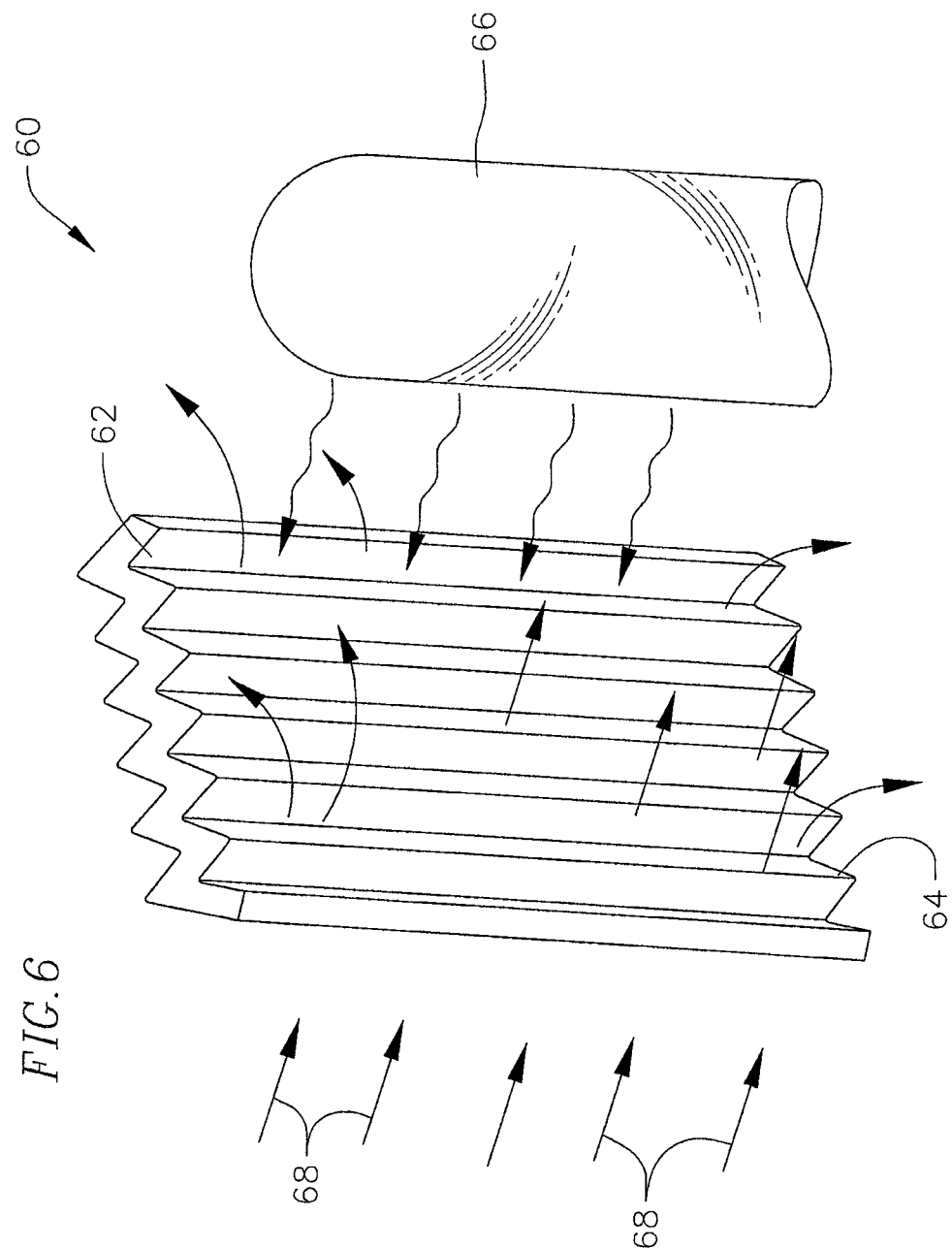
FIG. 6 is a stylized perspective view of a pleated PCO filter and a light source according to one embodiment of the present disclosure.

A second set of tests was conducted on two different PCO filters by introducing benzene, toluene, ethylbenzene, and xylenes (BTEX) into the Test Unit. In the first test, the reactor 12 of the closed-loop testing apparatus (see FIG. 2) contained a first PCO filter 50 having a support medium 52 which was fabricated into a flat, rectangular shape, as illustrated in FIG. 5 (i.e., the support medium 52 of the first PCO filter 50 was a rectangular parallelepiped). The flat PCO filter 50 also included a photocatalyst 54 attached to the support medium 52 and a UV light 56 configured to irradiate the photocatalyst 54. The support medium 52 of the flat PCO filter 50 was densely-packed and had an air permeability of less than approximately 155 $CFM/ft^2$. In the second test, the reactor 12 of the closed-loop testing apparatus (see FIG. 2) contained a second PCO filter 60 having a support medium 62 which was formed into a pleated shape, as illustrated in FIG. 6. The second PCO filter 60 also included a photocatalyst 64 attached to the support medium 62 and a UV light 66 configured to irradiate the photocatalyst 64. The pleated PCO filter 60 included the same densely-packed fibers as the support medium 52 of the flat PCO filter 50 (i.e., the support medium 62 of the pleated PCO filter 60 had an air permeability of less than approximately 155 $CFM/ft^2$). Although the flat and pleated PCO filters 50, 60, respectively, had the same peripheral linear dimensions (i.e., height and width), the surface area of the pleated PCO filter 60 was approximately 4 times greater than the surface area of the flat PCO filter 50 due to the pleats. All other system components and settings were identical between the two tests ((i.e., both the flat and pleated support members 52, 62, respectively, were coated with the same semiconductor catalyst (i.e., titanium dioxide and platinum), activated by the same UV lamps with the same intensity, and exposed to the same target compound (i.e., BTEX)).

Figure 7:
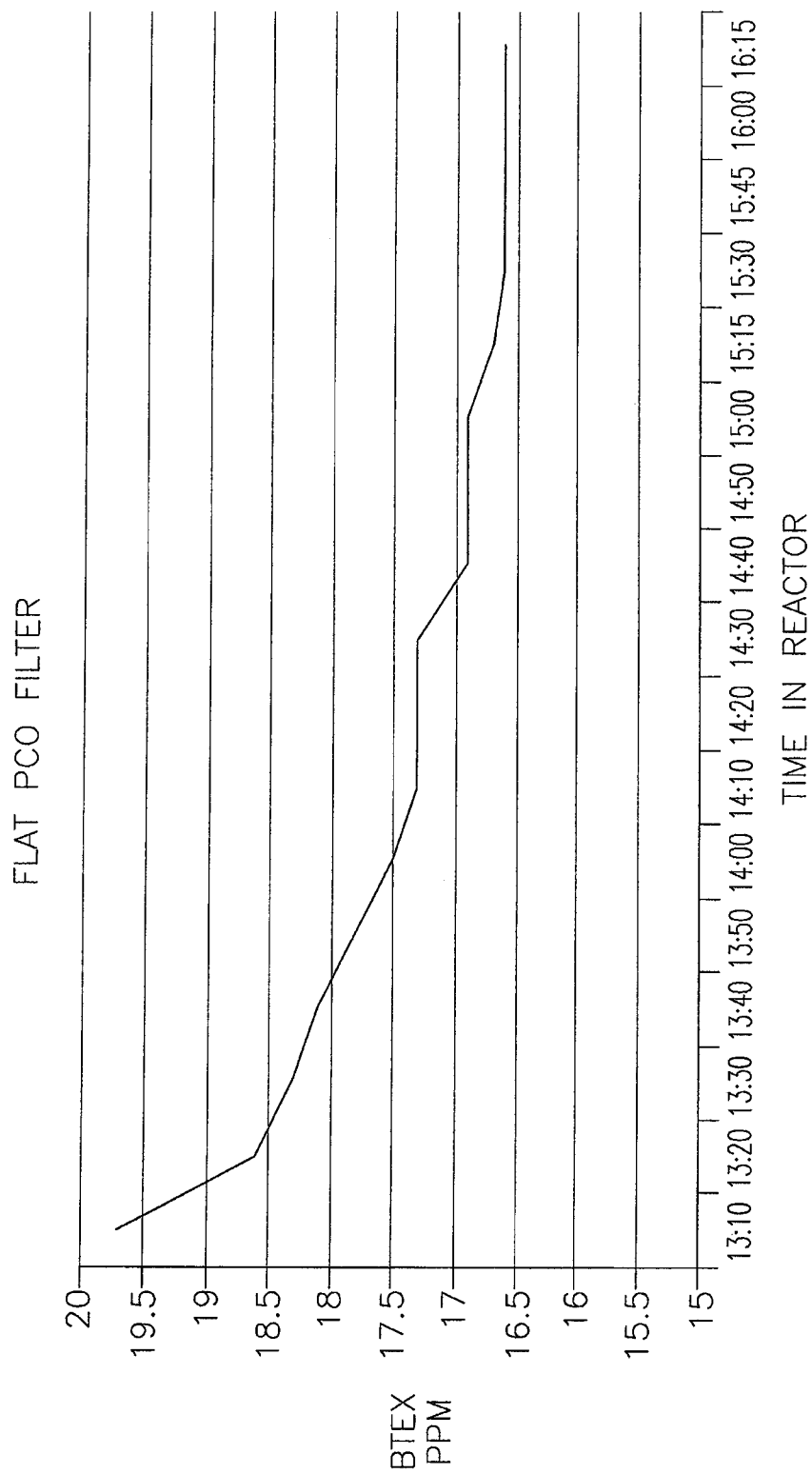
FIG. 7 is a graph showing testing results related to the performance of the flat PCO filter illustrated in FIG. 5.

As illustrated in FIG. 7, after circulating the airstream 58 through the flat PCO filter 50 for approximately 180 minutes, the concentration of BTEX in the system was reduced from approximately 19.8 ppm to approximately 16.5 ppm. Accordingly, the flat PCO filter 50 reduced the concentration of BTEX in the system at a rate of approximately 0.017 ppm/minute. In contrast, as illustrated in FIG. 8, after circulating the airstream 68 through the plated PCO filter 60 for approximately 78 minutes, the concentration of BTEX in the system was reduced from approximately 27 ppm to approximately 7.5 ppm. Accordingly, the pleated PCO filter 60 reduced the concentration of BTEX in the system at a rate of approximately 0.240 ppm/minute. Thus, the pleated PCO filter 60 of the present disclosure is configured to reduce the concentration of BTEX in an airstream at a rate approximately fourteen (14) times faster than the flat PCO filter 50.

Based upon the above-described test results, it is apparent that there is a non-linear relationship between the surface area of the PCO filter and the efficacy of the PCO filter in degrading (i.e., oxidizing) volatile organic compounds, such as BTEX.

Although not wishing to be bound by any particular theory, it is believed that the PCO filter having a pleated support member is capable of supporting a greater amount of photocatalyst (e.g., titanium dioxide and platinum) than an otherwise equivalent PCO filter having a flat support member (i.e., due to the presence of the pleats on the pleated PCO filter, the pleated PCO filter has a greater amount of photocatalyst and thus a greater number of active photocatalytic sites on the support medium). Thus, the greater number of active catalytic sites on the pleated PCO filter enabled the pleated PCO filter to degrade/oxidize target compounds within the airstream more quickly than an otherwise equivalent flat PCO filter (i.e., the greater amount of photocatalyst on the pleated PCO filter enabled the UV light to irradiate the photocatalyst and thereby generate a greater amount of hydroxyl radicals and super-oxide ions that are highly reactive with volatile organic compounds (VOCs) compared to an otherwise equivalent flat PCO filter).

While the present invention has been illustrated and described with reference to certain exemplary embodiments, those of ordinary skill in the art will understand that various modifications and changes may be made to the described embodiments without departing from the spirit and scope of the present invention, as defined in the following claims. Additionally, although relative terms have been used herein to describe a spatial relationship of one element to another, it is understood that these terms are intended to encompass different orientations of the various elements and components of the device in addition to the orientation depicted in the figures. Additionally, as used herein, the term "substantially" and similar terms are used as terms of approximation and not as terms of degree, and are intended to account for the inherent deviations in measured or calculated values that would be recognized by those of ordinary skill in the art.

What is claimed is:

1. A system, comprising:
 a closed-loop testing apparatus comprising:
  a photocatalytic reactor having an inlet and an outlet;
  a tank comprising toluene target compounds;
  a first pipe connecting an outlet of the tank to the inlet of the photocatalytic reactor; and
  a second pipe connecting the outlet of the photocatalytic reactor to an inlet of the tank; and
 a photocatalytic oxidation system in the photocatalytic reactor of the closed-loop testing apparatus, the photocatalytic oxidation system comprising:
 a filter comprising:
  a support medium comprising loosely-packed fibers; and
  a photocatalyst supported by the support medium, wherein the support medium has an air permeability of at least approximately 247 CFM/ft$^2$; and
 an ultraviolet light source configured to irradiate the photocatalyst with ultraviolet light,
 wherein, when the ultraviolet light source is turned on and the toluene target compounds are circulated from the tank through the photocatalytic reactor of the closed-loop testing apparatus, the irradiation of the photocatalyst photocatalytically oxidizes the toluene target compounds and reduces a concentration of the toluene target compounds in the closed-loop testing apparatus at a rate of at least 0.05 ppm/minute and by approximately 85% after approximately 90 minutes due to active catalytic sites on the support medium and the air permeability of the support medium.

2. The system of claim 1, wherein the support medium is a fibrous matte.

3. The system of claim 1, wherein the photocatalyst is titanium dioxide.

4. The system of claim 1, wherein the photocatalyst is metalized with a noble metal.

5. The system of claim 1, wherein the support medium is pleated.

6. The system of claim 1, wherein the support medium comprises fiberglass.

7. The system of claim 1, wherein the rate at which the irradiation of the photocatalyst is configured to reduce the concentration of the toluene target compounds in the closed-loop testing apparatus is approximately 0.24 ppm/minute due to the active catalytic sites on the support medium and the air permeability of the support medium.

* * * * *